(12) United States Patent
Heidemann et al.

(10) Patent No.: US 7,161,054 B2
(45) Date of Patent: Jan. 9, 2007

(54) PREPARATION OF OLIGOMERS OF ALKENES HAVING FROM 4 TO 8 CARBON ATOMS

(75) Inventors: Thomas Heidemann, Viernheim (DE); Armin Ulonska, Niederkirchen (DE); Bianca Stäck, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 266 days.

(21) Appl. No.: 10/775,064

(22) Filed: Feb. 11, 2004

(65) Prior Publication Data

US 2004/0181105 A1    Sep. 16, 2004

(30) Foreign Application Priority Data

Mar. 11, 2003 (DE) ............... 103 10 483

(51) Int. Cl.
  *C07C 2/10* (2006.01)
(52) U.S. Cl. ............... 585/531; 585/517; 585/503
(58) Field of Classification Search ............... 585/531, 585/517, 503
See application file for complete search history.

(56) References Cited

U.S. PATENT DOCUMENTS

| 5,177,282 | A |   | 1/1993 | Nierlich et al. |   |
|---|---|---|---|---|---|
| 6,846,965 | B1 | * | 1/2005 | Schulz et al. | ............... 585/510 |
| 2003/0130550 | A1 |   | 7/2003 | Schulz et al. |   |

FOREIGN PATENT DOCUMENTS

| DE | 39 148 17 | 11/1990 |
|---|---|---|
| WO | WO 99/25668 | 5/1999 |
| WO | 00/69795 | 11/2000 |
| WO | 01/72670 | 10/2001 |

OTHER PUBLICATIONS

Chauvel et al., Petrochemical Process, Edition Technip (1989), pp. 183-187.
Asinger et al., "Die petrolchemische Industrie", Akademie-Verlag (1971), pp. 278-299.

* cited by examiner

*Primary Examiner*—Thuan Dinh Dang
(74) *Attorney, Agent, or Firm*—Novak Druce & Quigg, LLP

(57) ABSTRACT

Process for preparing oligomers of alkenes having from 4 to 8 carbon atoms from a feed stream comprising such alkenes or hydrocarbon streams in which such alkenes are present over a nickel-containing, heterogeneous catalyst in n successive adiabatically operated reactors, where n is 2 or an integer greater than 2, at from 30 to 280° C. and pressures of from 1 to 300 bar, where the feed stream has a temperature $T_{in}$ when it enters the first reaction zone, experiences a temperature increase in each reaction zone and, if this temperature increase is more than $T_{in}+20°$ C., is brought to a temperature in the range $T_{in}\pm20°$ C. before it enters a subsequent reaction zone, wherein the feed stream is divided and the feed substreams obtained in this way are fed to the 2 reactors, or if more than 2 reactors are used to at least 2 of the reactors, with addition of fresh feed in such a way that the temperature in one of the reactors is at most 20° C. higher than that in each of the other reactors used.

5 Claims, 2 Drawing Sheets

PREPARATION OF OLIGOMERS OF ALKENES HAVING FROM 4 TO 8 CARBON ATOMS

Figure 1:
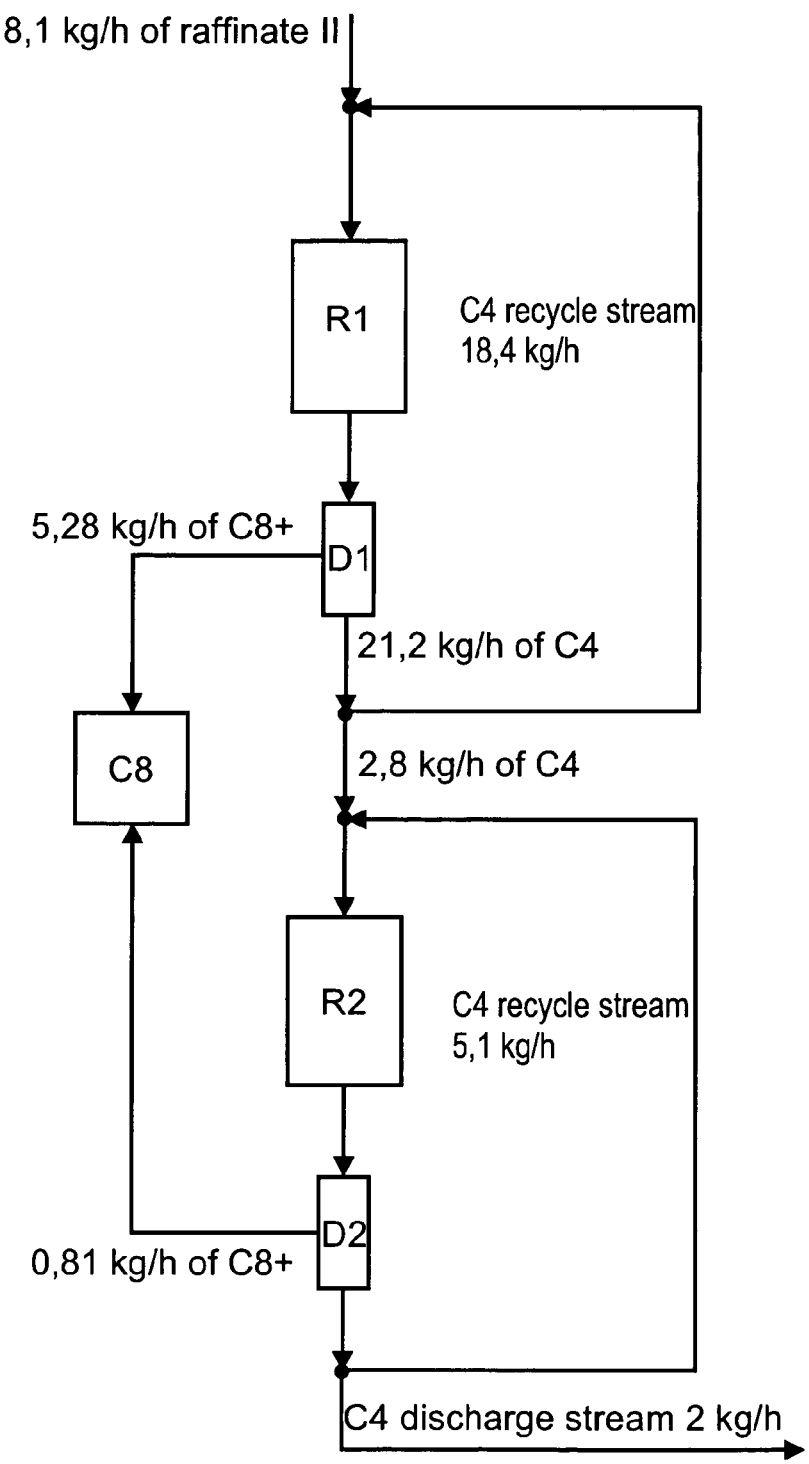

The present invention relates to a process for preparing oligomers of alkenes having from 4 to 8 carbon atoms from a feed stream comprising such alkenes or hydrocarbon streams in which such alkenes are present over a nickel-containing, heterogeneous catalyst in n successive adiabatically operated reactors, where n is 2 or an integer greater than 2, at from 30 to 280° C. and pressures of from 1 to 300 bar, where the feed stream has a temperature $T_{in}$ when it enters the first reaction zone, experiences a temperature increase in each reaction zone and, if this temperature increase is more than $T_{in}+20°$ C., is brought to a temperature in the range $T_{in}\pm 20°$ C. before it enters a sub-sequent reaction zone.

Alkenes having from 2 to 8 carbon atoms or mixtures thereof are available in large quantities both from FCC (fluidized catalytic cracking) plants and from steam crackers. Use of the $C_4$ fraction, i.e. a mixture consisting essentially of butenes and butanes, if desired after separating off the isobutene, for preparing oligomers, in particular octenes and dodecenes, is known. Both the octenes and the dodecenes can be hydroformylated and subsequently hydrogenated to give the corresponding alcohols which can then be used, for example, for preparing plasticizers or surfactants.

The oligomerization is carried out industrially in the presence of either homogeneous or heterogeneous catalysts. The most important heterogeneously catalyzed alkene oligomerization processes employed in industry are described, for example, in A. Chauvel and G. Lefebvre, Petrochemical Process, Edition Technip (1989), pp. 183–187 and F. Asinger, "Die petrolchemische Industrie", Akademie-Verlag (1971), pp. 278–299.

The oligomerization of alkenes normally proceeds exothermically over a heterogeneous catalyst. The temperature of the reaction mixture thus generally increases gradually during passage through the reaction zone. Due to the lower capital costs associated therewith, preference is frequently given to carrying out the oligomerization in adiabatically operated reactors.

In such reactions, the catalyst activity frequently decreases with time, i.e. with the elapsed productive operating time. In particular, there appears to be a proportional relationship between the heat of reaction evolved in productive operation over the catalyst and the decrease in catalyst activity. [lacuna] the catalyst activity in the oligomerization reaction zone normally decreases, which can be partially compensated by increasing the temperature at the catalyst.

The temperature in the reaction zone can be controlled by means of the initial temperature of the reaction mixture. It has to be high enough to achieve the desired catalyst activity and reaction rate, which generally have a critical influence on the conversion. Furthermore, to save energy, preference is given to an inlet temperature in the vicinity of ambient temperature.

When the maximum permissible temperature has been reached, the activity of the catalyst cannot usually be increased further via the temperature alone; furthermore, an upper limit on the temperature of the reaction mixture is frequently imposed in practice by the maximum permissible pressure in the reactor.

WO-A 01/72670 discloses a process for the oligomerization of alkenes, in which part of the output from the pseudoisothermally operated reactor is worked up to give the end product and the other part, which has not been worked up, is recirculated to the reactor together with fresh feed. However, the lack of a work-up step results in an accumulation of by-products, in particular oligomers, in the feed stream.

WO-A 00/69795 describes a process for the oligomerization of alkenes, in which the volume of the individual reaction zones is set so that the temperatures of the reaction mixtures leaving two different reaction zones differ by not more than 20° C. However, the temperature control via the reactor volumes restricts this process in terms of apparatus to a very particular mode of operation.

In the processes presented, the time for which a particular catalyst can be used productively has a critical influence on the economics of the entire process, so that the chemical industry continues to be interested in developing catalysts having a pro-longed life and improved processes matched to these catalysts.

It is an object of the present invention to provide a process for the oligomerization of alkenes, in which the operating life of the catalyst is increased by means of improved use of the feed.

We have found that this object is achieved by a process for preparing oligomers of alkenes having from 4 to 8 carbon atoms from a feed stream comprising such alkenes or hydrocarbon streams in which such alkenes are present over a nickel-containing, heterogeneous catalyst in n successive adiabatically operated reactors, where n is 2 or an integer greater than 2, at from 30 to 280° C. and pressures of from 1 to 300 bar, where the feed stream has a temperature $T_{in}$ when it enters the first reaction zone, experiences a temperature increase in each reaction zone and, if this temperature increase is more than $T_{in}+20°$ C., is brought to a temperature in the range $T_{in}\pm 20°$ C. before it enters a subsequent reaction zone, wherein the feed stream is divided and the feed substreams obtained in this way are fed to the 2 reactors, or if more than 2 reactors are used to at least 2 of the reactors, with addition of fresh feed in such a way that the temperature in one of the reactors is at most 20° C. higher than that in each of the other reactors used.

For the purposes of the present invention, "oligomers" are dimers, trimers and higher oligomeric products having up to 18, preferably up to 12 and particularly preferably up to 8, carbon atoms formed by reaction of alkenes having from 4 to 8 carbon atoms.

For the purposes of the present invention, the term "feed" is used as a collective term for starting materials which comprise reactive alkenes and are fed to the reactors.

The term "operating life of the catalyst" refers to the entire time for which a catalyst is used in the oligomerization of alkenes. During this period of use, the catalytic activity generally decreases. The catalyst is normally replaced when its residual activity has dropped to a level at which the process is no longer economical.

An "adiabatic reaction mode" is, in the engineering sense, a mode of operation in which the entire heat of reaction except for the part of the heat of reaction which is given off to the environment by natural thermal conduction and radiation of heat from the reactor is taken up by the reaction mixture and is removed from the reactor together with this.

Among alkenes having from 2 to 8 carbon atoms which can be converted into oligomers using the process of the present invention, preference is given to the singly unsaturated butenes, pentenes and hexenes. Particular preference is given to the individual compounds 1-butene, 2-butene, 1-pentene, 2-pentene, 1-hexene or 3-hexene.

Suitable feeds for the process of the present invention are feeds whose content of alkene or alkenes is normally from 5 to 100% by weight, preferably from 30 to 100% by weight and particularly preferably from 50 to 100% by weight.

The process of the present invention is very particularly useful for the reaction of alkenes which are present in admixture with alkanes, with the alkenes and alkanes mostly having, in particular, four carbon atoms each. Suitable $C_4$-hydrocarbon streams of this type are, for example, mixtures having the following composition:

| | |
|---|---|
| butanes | from 10 to 90% by weight |
| butenes | from 10 to 90% by weight, | where the butene fraction can have the following composition:

| | |
|---|---|
| 1-butene | from 1 to 50% by weight |
| cis-2-butene | from 1 to 50% by weight |
| trans-2-butene | from 1 to 99% by weight |
| isobutene | from 1 to 5% by weight. |

A particularly preferred feed is raffinate II. This is a butene-containing $C_4$-hydrocarbon mixture as is obtained from the $C_4$ fraction from crackers by separating off more highly unsaturated hydrocarbons such as dialkenes, in particular 1,3-butadiene, or acetylene and subsequently isobutene. A typical composition of raffinate II is:

| | |
|---|---|
| isobutane, n-butane | 26% by weight |
| isobutene | 1% by weight |
| 1-butene | 26% by weight |
| trans-2-butene | 31% by weight |
| cis-2-butene | 16% by weight. |

The feeds can be freed of butadiene and sulfur-containing and oxygen-containing compounds such as alcohols, aldehydes, ketones or ethers by hydrogenation or absorption on molecular sieves as described in DE-A 39 14 817 prior to the reaction.

Catalysts used are nickel-containing heterogeneous catalysts, preferably those having a high selectivity to linear oligomers. Such nickel-containing catalysts are known to those skilled in the art, for instance from WO-A 01/72670.

The Ni catalysts are preferably located in a fixed bed and are preferably in the form of shaped bodies: e.g. pellets (5 mm×5 mm, 5 mm×3 mm, 3 mm×3 mm), rings (7 mm×7 mm×3 mm, 5 mm×5 mm×2 mm, 5 mm×2 mm×2 mm) or extrudates or star extrudates (1.5 mm diameter, 3 mm diameter, 5 mm diameter). The above quoted sizes and types of shaped bodies are purely by way of example and do not restrict the scope of the present invention.

It is possible to use the same catalyst or different nickel-containing catalysts in the individual reactors of the reactor cascade.

The reactors employed are normally cylindrical reactors which are charged with the nickel-containing catalyst and contain no additional internals.

The oligomerization reaction generally takes place at from 30 to 280° C., preferably from 30 to 140° C. and in particular from 40 to 130° C., and a pressure of generally from 1 to 300 bar, preferably from 5 to 100 bar and in particular from 20 to 70 bar. The pressure is advantageously chosen so that the feed stream is supercritical and in particular liquid at the temperature set.

Different reaction conditions in respect of pressure and/or temperature within the abovementioned pressure and temperature ranges can be set in the individual reactors of the reactor cascade.

After leaving a reactor, the respective crude product stream is worked up in a manner known per se, preferably by distillation, to separate off the oligomers formed. Part of the residual stream comprising unreacted alkenes and possibly accompanying alkanes is recirculated as recycled stream to the same reactor and the remainder is passed, together with the required further stream of fresh feed, to the next reactor.

After reaction in the last reactor, the alkene content of the residual stream is generally from 5 to 20% by weight; part of the residual stream is used further as recycle stream and the remainder is discharged from the process.

Residual streams (recycled streams) and feed substreams can be brought to the desired temperature using apparatuses customary for this purpose, e.g. heat exchangers, before introduction into a reactor.

The ratio in which the stream of fresh feed and the respective residual stream are introduced into the next reactor can readily be determined by a person skilled in the art by means of simple preliminary tests and consideration of the temperature to be set in this next reactor.

Feed substream and recirculated residual stream can be fed into the reactor simultaneously and separately, for instance via separate lines, or after prior mixing.

In the process of the present invention, the conversion to the desired oligomers is generally from 10 to 100%, preferably from 50 to 100%, based on the alkenes used.

A person skilled in the art will be familiar with the other details of how the process is carried out, especially from WO-A 99/25668, WO-A 01/72670 and WO-A 00/69795, which are hereby fully incorporated by reference.

The process of the present invention has the advantage that the temperature stress on the catalysts in the various reactors is leveled out. This generally increases the operating life of those catalysts which as a result can be operated at a lower temperature. Accordingly, there are comparable decreases in the catalyst activity in the reactors, so that replacement of the catalyst in all reactors at the same time becomes more economical.

EXAMPLES

The feed employed in Examples 1 and 2 was in each case 8.1 kg/h of raffinate II having the composition: 5% by weight of isobutane, 18% by weight of n-butane, 31% by weight of 1-butene, 2% by weight of isobutene, 28% by weight of trans-2-butene, 16% by weight of cis-2-butene.

The experiments were carried out in a two-stage adiabatic reactor cascade over a catalyst as described in DE-A 43 39 713, Example 2. The first reactor had a volume of 40 liters, and the second had a volume of 20 liters. After the first reactor and the second reactor, $C_{8+}$-alkene (alkene having two or more butene units) formed was separated by distillation from unreacted $C_4$-alkene or inert $C_4$-alkane. Part of the $C_4$-hydrocarbon stream which had been separated off in this way was used further, as specified in more detail in Examples 1 and 2 below.

Figure 2:
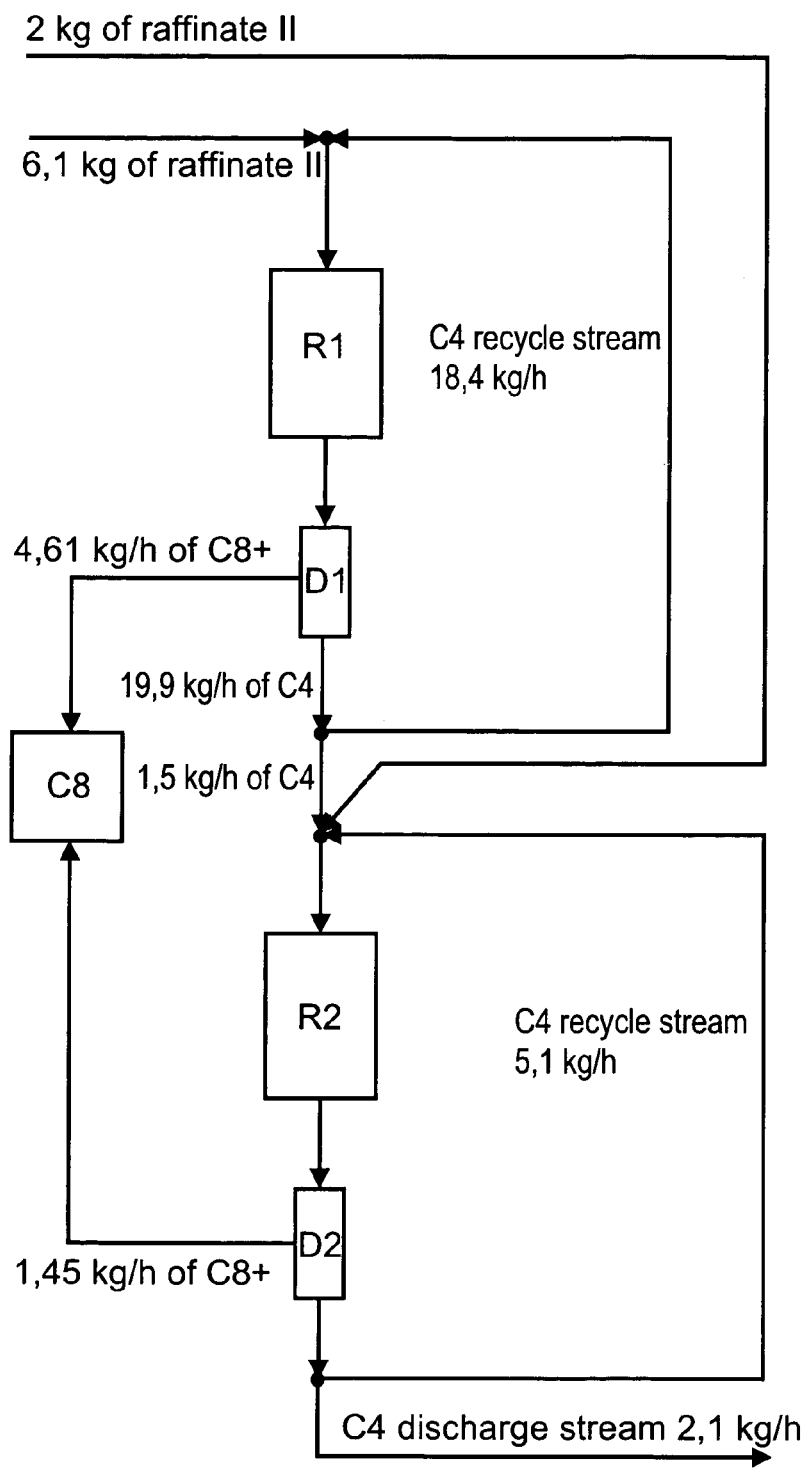

Streams and apparatus of Examples 1 and 2 are shown schematically in FIG. 1 and FIG. 2. In the figures:

R1=reactor 1
R2=reactor 2
D1=distillation column 1
D2=distillation column 2.

Example 1

Comparative Example, FIG. 1

8.1 kg/h of raffinate II as feed were mixed with 18.4 kg/h of recycled stream from reactor 1, introduced at an inlet temperature of 20° C. into the reactor 1 and reacted there. The reaction mixture heated up by 54° C. to 74° C. at the reactor outlet.

The output from reactor 1 was separated by distillation into 5.28 kg/h of bottom product (>99% by weight of $C_{8+}$) and 21.2 kg/h of top product (>99% by weight of $C_4$). 18.4 kg/h of this top product formed the recycled stream to reactor 1.

The remaining 2.8 kg of the top product were mixed with 5.1 kg of recycled stream from reactor 2, introduced at a reactor inlet temperature of 40° C. into the reactor 2 and reacted there.

The reaction mixture heated up by 25° C. to 65° C. at the reactor outlet.

The output from reactor 2 was separated by distillation into 0.81 kg/h of bottom product (>99% by weight of $C_{8}+$) and 7.1 kg/h of top product. 5.1 kg of this top product formed the recycled stream from reactor 2; the remaining 2 kg/h were discharged from the experiment.

Analysis of the combined bottom products indicated a $C_{8+}$ selectivity ($Sel_{C8+}$) of 82%. The total butene conversion ($C_{butenes}$) was 97.9%.

Example 2

Example According to the Present Invention, FIG. 2

The 8.1 kg/h of raffinate II were divided into two streams of 6.1 kg/h and 2 kg/h.

The stream comprising 6.1 kg/h of raffinate II was mixed with 18.4 kg/h of recycled stream from reactor 1, introduced at an inlet temperature of 20° C. into the reactor 1 and reacted there. The reaction mixture heated up by 45° C. to 65° C. at the reactor outlet.

The output from reactor 1 was separated by distillation into 4.61 kg/h of bottom product (>99% by weight of $C_{8+}$) and 19.9 kg/h of top product (>99% by weight of C4). 18.4 kg/h of this top product formed the recycled stream to reactor 1.

The remaining 1.5 kg of the top product were mixed with the 2 kg/h of fresh raffinate II mentioned at the beginning of this Example 2 and 5.1 kg of recycled stream from reactor 2, introduced at a reactor inlet temperature of 25° C. into the reactor 2 and reacted there.

The reaction mixture heated up by 40° C. to 65° C. at the reactor outlet.

The output from reactor 2 was separated by distillation into 1.45 kg/h of bottom product (>99% by weight of $C_{8+}$) and 7.2 kg/h of top product. 5.1 kg of this top product formed the recycle stream from reactor 2; the remaining 2.1 kg/h were discharged from the experiment.

Analysis of the combined bottom products indicated a $C_{8+}$ selectivity $Sel_{C8+}$ of 82%. The total butene conversion $C_{butenes}$ was 97.4%.

Evaluation of Examples 1 and 2

| Example | $T_{R1in}$ [° C.] | $T_{R1out}$ [° C.] | $\Delta T_{R1out-R1in}$ [° C.] | $T_{R2in}$ [° C.] | $T_{R2out}$ [° C.] | $\Delta T_{R2out-R2in}$ [° C.] | $C_{butenes}$ [%] | $Sel_{C8+}$ |
|---|---|---|---|---|---|---|---|---|
| 1 | 20 | 74 | 54 | 40 | 65 | 25 | 97.9 | 82 |
| 2 | 20 | 65 | 45 | 25 | 65 | 40 | 97.4 | 82 |

$T_{R1in}$ Temperature at the inlet of reactor R1
$T_{R1out}$ Temperature at the outlet of reactor R1
$\Delta T_{R1out-R1in}$ Difference between the outlet and inlet temperatures of reactor R1
$T_{R2in}$ Temperature at the inlet of reactor R2
$T_{R2out}$ Temperature at the outlet of reactor R2
$\Delta T_{R2out-R2in}$ Difference between the outlet and inlet temperatures of reactor R2
$C_{butenes}$ Total butene conversion
$Sel_{C8+}$ $C_{8+}$ selectivity The division of the feed in Example 2 according to the present invention led to an evening out of the temperature stress on the catalysts in the reactors R1 and R2, which leads to an increased operating life of the catalyst. The conversion of butenes ($C_{butenes}$) and the $C_{8+}$ selectivity ($Sel_{C8+}$) remained virtually unchanged compared to the mode of operation of Example 1.

We claim:

1. A process for preparing oligomers of alkenes having from 4 to 8 carbon atoms from a feed stream comprising such alkenes or hydrocarbon streams in which such alkenes are present over a nickel-containing, heterogeneous catalyst in n successive adiabatically operated reactors, where n is 2 or an integer greater than 2, at from 30 to 280° C. and pressures of from 1 to 300 bar, where the feed stream has a temperature $T_{in}$ when it enters the first reaction zone, experiences a temperature increase in each reaction zone by more than $T_{in}+20°$ C. and is brought to a temperature in the range $T_{in}\pm20°$ C. before it enters a subsequent reaction zone, wherein the feed stream is divided and the feed substreams obtained in this way are fed to the 2 reactors, or in the event that more than 2 reactors are used to at least 2 of the reactors, with addition of fresh feed in such a way that the temperature in one of the reactors is at most 20° C. higher than that in each at the other reactors used.

2. A process as claimed in claim 1, wherein $T_{in}$ is in the range from 20 to 120° C.-

3. A process as claimed in claim 1, wherein the temperature in one of the reactors is at most 10° C. higher than that in each of the other reactors used.

4. A process as claimed in claim 1, wherein the proportion of oligomers in the feed stream and in the feed substreams does not exceed 30% by weight.

5. A process as claimed in claim 1, wherein the feed stream and the feed substreams is/are reacted in condensed form.

* * * * *

UNITED STATES PATENT AND TRADEMARK OFFICE
CERTIFICATE OF CORRECTION

PATENT NO. : 7,161,054 B2 Page 1 of 1
APPLICATION NO. : 10/775064
DATED : January 9, 2007
INVENTOR(S) : Heidemann et al.

It is certified that error appears in the above-identified patent and that said Letters Patent is hereby corrected as shown below:

In Column 6, indicated line 67, "C.-" should read --C.--

Signed and Sealed this

Eighth Day of April, 2008

JON W. DUDAS
*Director of the United States Patent and Trademark Office*